United States Patent [19]

Glad et al.

[11] Patent Number: 5,255,564

[45] Date of Patent: Oct. 26, 1993

[54] APPARATUS FOR THE DISCRIMINATION OF CHEMICAL LIQUIDS VIA SOUND SPEED MEASUREMENTS

[75] Inventors: Wayne Glad, Chula Vista; Robert K. Fogg, Jr., San Diego, both of Calif.

[73] Assignee: The United States of America as represented by the secretary of the Navy, Washington, D.C.

[21] Appl. No.: 750,141

[22] Filed: Aug. 22, 1991

[51] Int. Cl.$^5$ .......................................... G01N 29/18
[52] U.S. Cl. .................................. 73/597; 73/64.53; 73/61.79
[58] Field of Search ............... 73/24.05, 24.01, 61.79, 73/64.53, 597

[56] References Cited

U.S. PATENT DOCUMENTS

| | | | |
|---|---|---|---|
| 3,791,200 | 2/1974 | Hayre | 73/61.79 |
| 3,817,098 | 6/1974 | Brown | 73/194 A |
| 3,987,674 | 10/1976 | Baumoel | 73/194 A |
| 4,011,753 | 3/1977 | Hausler | 73/194 A |
| 4,114,439 | 9/1978 | Fick | 73/194 A |
| 4,145,917 | 3/1979 | Brazhnikov et al. | 73/64.53 |
| 4,242,744 | 12/1980 | Rottmar | 367/173 |
| 4,331,025 | 5/1982 | Ord, Jr. | 73/54 |
| 4,389,899 | 6/1983 | Krause | 73/861.28 |
| 4,417,481 | 11/1983 | Krause | 73/861.28 |
| 4,478,088 | 10/1984 | Loveland | 73/861.28 |
| 4,509,372 | 4/1985 | Mount | 73/861.28 |
| 4,555,932 | 12/1985 | Crosby, Jr. | 73/24.01 |
| 4,583,410 | 4/1986 | O'Neil | 73/861.28 |
| 4,630,482 | 12/1986 | Traina | 73/861.28 |
| 4,663,961 | 5/1987 | Nelson et al. | 73/61.79 |
| 4,748,857 | 6/1988 | Nakagawa | 73/861.28 |
| 4,754,650 | 7/1988 | Smalling et al. | 73/861.28 |

FOREIGN PATENT DOCUMENTS

| | | | |
|---|---|---|---|
| 0145961 | 1/1981 | Fed. Rep. of Germany | 73/24.05 |
| 1281994 | 1/1987 | U.S.S.R. | 73/597 |
| 2167185 | 5/1986 | United Kingdom | 73/64.53 |

OTHER PUBLICATIONS

"Sound Velocity Measurements on Castings and Ceramics"; Parimetrics Product Literature: *Ultrasonic Thickness Gages and Their Applications,;* Model 5252; Jan. 1989.

*Primary Examiner*—Hezron E. Williams
*Assistant Examiner*—Rose M. Finley
*Attorney, Agent, or Firm*—Harvey Fendelman; Thomas Glenn Keough; Michael A. Kagan

[57] ABSTRACT

An apparatus is provided for identifying an unknown liquid by determining the speed of sound in the liquid. A pulse generator provides an excitation pulse to a first acoustic transducer which transmits an acoustic pulse in the liquid. The acoustic pulse is received by a second acoustic transducer at a distance from the first transducer measured by a displacement transducer. A gated clock is enabled by the excitation pulse and disabled when the acoustic pulse received by the second acoustic transducer reaches a predetermined threshold. The clock measures the time it takes the acoustic pulse to travel the distance between transducers. The temperature of the liquid is determined by indirect means and is provided as an input to a digital computer which computes the speed of the acoustic pulse by dividing the distance between the transducers, provided by the displacement transducer, by the elapsed time measured by the clock. The computer compares the speed of the unknown liquid with the sound speeds of known liquids at the temperature of the unknown liquid. A display coupled to the computer presents the identities of any of the known liquids having the sound speeds within a predetermined interval about the calculated sound speed.

2 Claims, 3 Drawing Sheets

APPARATUS FOR THE DISCRIMINATION OF CHEMICAL LIQUIDS VIA SOUND SPEED MEASUREMENTS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to the measurement of the speed of sound in liquids, and more particularly to identifying an unknown liquid by determining the speed of sound in the liquid and correlating the speed with known liquids having known speeds of sound.

There are many applications where identification of liquids in bulk containers is required. One example of such an application is the identification of liquid filled containers located in industrial storage yards or waste sights. For example, the United States Customs Department has the need to identify may types of bulk liquids at U.S. ports of entry for purposes that include export control or identification of contraband.

Presently, identification of liquids stored in sealed containers, such as 55 gallon steel drums, requires breaching the integrity of the container and physically sampling the liquid. However, opening a container and performing the tests necessary to identify the liquid content is very time consuming and potentially dangerous. Exposure to many of the liquids encountered in such inspections may present hazards to human health. Therefore, a need exists for a simple non-contact method for identifying such liquids.

SUMMARY OF THE INVENTION

The present invention provides an apparatus for identifying an unknown liquid by determining the speed of sound in the liquid. A pulse generator provides an excitation pulse to a first acoustic transducer acoustically coupled to the liquid which transmits an acoustic pulse in the liquid. The acoustic pulse is received by a second acoustic transducer at a distance from the first transducer measured by a displacement transducer. A gated clock is enabled by the excitation pulse and disabled when the acoustic pulse received by the second acoustic transducer reaches a predetermined threshold. The clock measures the time it takes the acoustic pulse to travel the distance between transducers. The temperature of the liquid is determined by indirect means and is provided as an input to a digital computer which computes the speed of the acoustic pulse by dividing the distance between transducers by the elapsed time measured by the clock. The computer compares the speed of the unknown liquid with the sound speeds of known liquids at the temperature of the unknown liquid. A display coupled to the computer presents the identities of any of the known liquids having the sound speeds within a predetermined interval about the calculated sound speed.

An advantage of the present invention is that it provides a way of easily identifying an unknown liquid, typically stored within a sealed container, without requiring direct sampling of the liquid. Another advantage of the invention is that it can easily provide an indirect way of indicating that an unknown liquid is not a particular substance. The invention avoids the necessity of requiring direct sampling of the unknown liquid and eliminates human exposure to chemical liquids that may present health hazards.

DESCRIPTION OF THE PREFERRED EMBODIMENT

The speed of sound in a liquid substance depends on the mechanical properties of the substance. These mechanical properties are influenced by the molecular structure of the substance and the way that the molecules aggregate in the liquid phase. Consequently, the speed of sound varies from substance to substance. A review of the sound speed literature indicates that this variance can be significant, as for example, by as much as a factor of two between ethyl ether and glycerol. Even among more chemically similar substances, the sound speeds can vary by as much as a few percent. Table I presents the speed of sound for some selected liquids. As can be seen, most of the sound-speeds are distributed between 1000 and 2000 meters/second.

TABLE I

| Speed of Sound of Selected Compounds At 25° C. | |
|---|---|
| Compound | Speed of Sound (meters/second) |
| Acetone | 1174 |
| Benzene | 1295 |
| Ethyl Ether | 985 |
| Ethanol | 1207 |
| Ethylene Glycol | 1658 |
| Glycerol | 1904 |
| Kerosene | 1324 |
| Methanol | 1103 |
| Water (distilled) | 1497 |
| Water (sea) | 1531 |

The speed of sound in a liquid depends on its density and compressibility. This means that molecules of similar size and structure may have similar sound-speeds, although it does not prevent significantly different compounds from having similar sound-speeds. Therefore, the correlation of sound-speeds to compounds is largely an empirical process.

Figure 1:
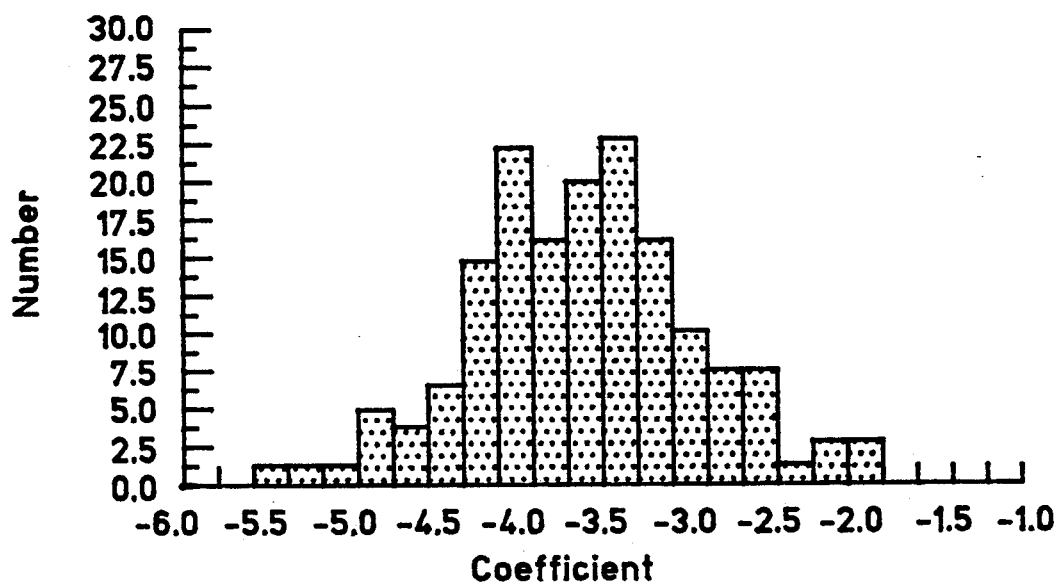
FIG. 1 is a histogram of the temperature dependence of the speeds of sound of various liquids.

The speed of sound of most liquids shows a significant temperature dependence. For most organic compounds, the slope of the sound speed versus temperature curve is negative, and the curve is linear from 0° to 70° C. FIG. 1 is a histogram of the linear coefficient of temperature dependence of speed of sound for a number of organic compounds. As can be seen, the coefficients range from $-6$ to $-1$ m/(s$-$°C.). The average for the compounds depicted in FIG. 1 is about $-3.5$ m/(s$-$°C.). Water is anomalous: the temperature correction coefficient is positive and the temperature dependence of sound speed is not as linear as it is for most organic compounds, although the order of magnitude of the coefficient is about the same. Note that a 5° C. change in temperature results in about a 1% change in the speed of sound for an average compound. Therefore, temperature should be taken into account when using sound velocities in order to accurately discriminate between substances using sound speed measurements. The ability to discriminate one compound from another via a sound speed measurement thus depends on the accuracy of the measurement and the accuracy of the database of known sound-speeds and temperature correction coefficients.

Figure 2A:
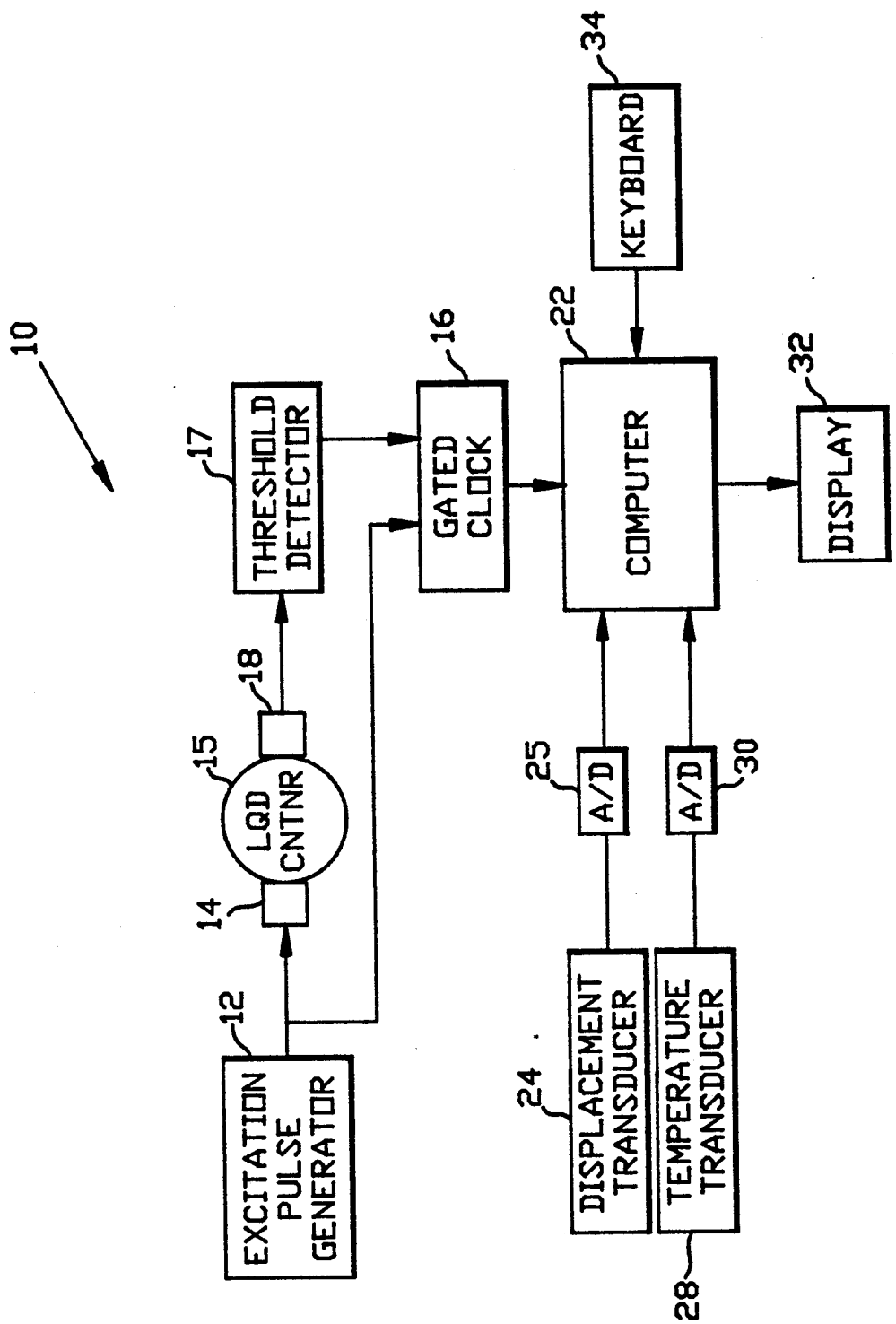
FIG. 2A is a block diagram of one apparatus for identifying an unknown liquid by determining the speed of sound of the liquid.

Referring to FIG. 2A which presents a block diagram of an apparatus 10 for discriminating chemical liquids based on sound speed measurements, there is shown excitation pulse generator 12 which provides an electrical excitation pulse having a predetermined pulse width and amplitude to excitation transducer 14. The electrical pulse is converted by transducer 14 into an acoustic pulse having a corresponding waveform. Transducer 14 is acoustically mounted to container 15. By way of example, a contact gel such as Aquasonic 100 Ultrasound Transmission Gel by Parker Laboratories, Inc. interposed between transducer 14 and container 15 has been shown to provide good acoustic coupling therebetween. However, other methods of achieving good acoustic coupling between container 15 and transducer 14 may also be used, as for example, by using water jets or rubber compounds.

The pulse output by excitation pulse generator 12 enables gated clock 16, preferably operating at a frequency of at least 1 MHz. Clock 16 begins to operate a counter upon receipt of the excitation pulse. The acoustic pulse generated by excitation transducer 14 traverses the liquid stored in container 15 and is received by receiver transducer 18 which is also acoustically coupled to container 15 in a manner similar to that of transducer 14. Transducer 18 converts the acoustic pulse into an analog electrical output which is provided to threshold detector 20. By way of example, transducers 14 and 18 may be Physical Acoustic Group R15 SN 9404 piezoelectric transducers. The excitation pulse width and amplitude are chosen largely to maximize the signal to noise level of the output of excitation pulse generator 12 by attempting to match the pulse width to the resonant frequency of transducers 12 and 14, as would be well known to those skilled in this art. By way of example, in the preferred embodiment, a pulse width of 10–100 microseconds would be expected to provide satifactory results with the specific transducer used.

When the output of threshold detector 17 reaches a predetermined threshold, clock 16 is disabled. In this case, a detectable signal above the noise with a given slope triggers detector 20. Clock 16 provides a value to computer 22 corresponding to the period of time during which the counter of clock 16 is enabled. Computer 22 may, for example, be a DOS based personal computer.

Figure 2B:
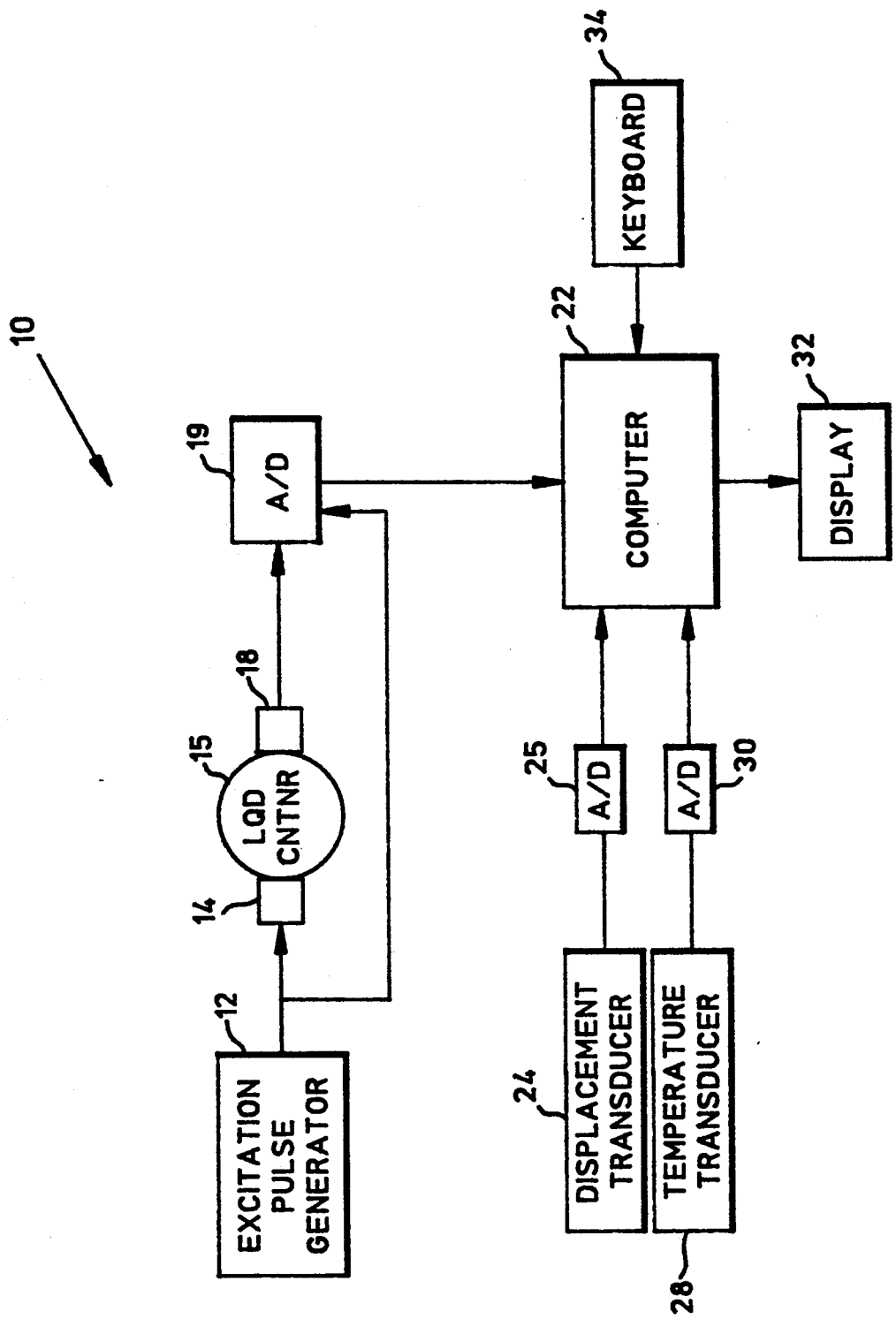
FIG. 2B is a block diagram of a second apparatus for identifying an unknown liquid by determining the speed of sound of the liquid.

An alternative method for determining the speed of the acoustic pulse is described below with reference to the apparatus depicted in FIG. 2B. The analog output of receiving transducer 18 is transformed by analog-to-digital (A/D) converter 19 into a digitized representation of the acoustic signal received by transucer 18. A/D converter 19 is enabled by the pulse provided by excitation pulse generator 12. The digitized reperesentation is provided as data to computer 22. Software implemented in computer 22 stores and examines the data to determine when the digitized signal level reaches a given percentage of the maximum signal amplitude received by receiver transducer 18. Computer 22 determines the maximum signal level of the stored waveform, and then finds the data point of the wave-form where a certain percentage of this maximum level is first reached. The acoustic transit time is the point number of this data point divided by the data acquisition rate of the A/D converter. A typical data acquisition rate would be in the range of 5-25 MHz.

Typically, container 15 would be a 55 gallon steel drum, although it is contemplated that the present invention will be used to identify liquids in other types of fluid containers.

Figure 3:
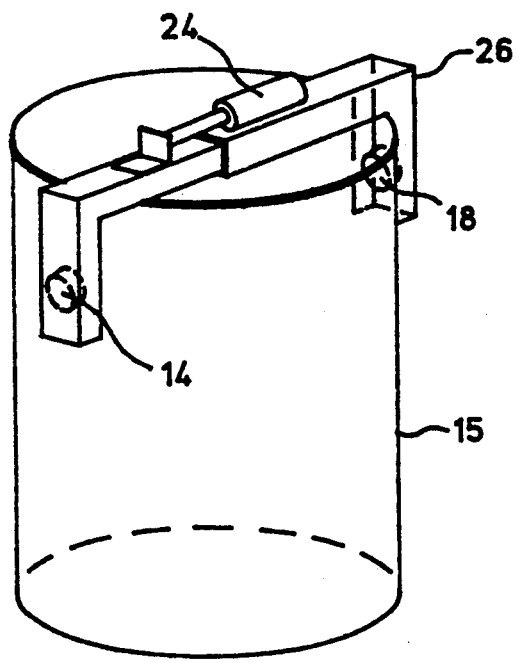
FIG. 3 shows the acoustic transducers of one embodiment of the present invention mounted about a bulk liquid container using an external caliper having a displacement transducer which measures the distance between transducers.

Referring to FIG. 3, an output corresponding to the distance between transducers, i.e., the distance traversed by the acoustic pulse through the unknown liquid, is provided by a displacement transducer 24, such as a linear variable differential transformer or a linear potentiometer. Transducer 24 is mounted to adjustable external caliper 26 which is positioned about container 15 and adjusted so that excitation transducer 14 and receiver transducer 18 are in contact with and acoustically coupled to container 15. The analog output of displacement transducer 24 is signal conditioned and digitized by analog to digital converter 25 and provided to computer 22.

In a typical application of the present invention, the temperature of the liquid to be identified within container 15 is inferred through indirect techniques, as for example, by placing a temperature transducer 28, such as a thermocouple or thermistor, in thermal contact with container 15. This method assumes that the temperature of the exterior surface of the container equals the temperature of the liquid contained therein. Another indirect method would be to assume that the contents of the container and ambient air are in thermal equilibrium. In this case, the air temperature, which is easily measured, would correspond to the temperature of the liquid. However, it is to be understood that the scope of the invention also includes making direct temperature measurements of the unknown liquid, although this would require breach of the integrity of the container. The analog output of temperature transducer 28 is signal conditioned by an amplifier, not shown, digitized by A/D converter 30, and then provided as an input to computer 22. Signal conditioning the output of a transducer is well known by those skilled in this technology. Computer 22 calculates the speed of the acoustic pulse (sound speed) through the liquid by dividing the distance between transducers 14 and 18 by the elapsed time provided by gated clock 16. This experimentally determined speed of sound in the unknown liquid is referred to as the "calculated" sound speed. The use of the calculated sound speed to identify the unknown liquid is described in the paragraphs below.

The computer program implemented in computer 22 calculates a temperature corrected sound speed for each liquid in a data base having known ("reference") sound speeds at a specific ("reference") temperature and known temperature correction coefficients, "C." The temperature corrected sound speed is the speed of sound in each liquid at the temperature of the unknown liquid. Because the speed of sound through a liquid is temperature dependent, there arises the necessity of comparing the calculated sound speed with the speeds of sound of known liquids. In order to compensate for dependence of sound speed on temperature, the temperature of the unknown liquid is used as a variable input to modify the reference speed of each chemical liquid in the data base so that the calculated sound speed can be compared to a temperature corrected sound speed for each liquid identified in the data base. Then, the program compares the temperature corrected sound speeds with the calculated sound speed. Liquids having sound speeds within a predetermined margin of error about the calculated sound speed are identified on display 32 as potential candidates for the identity of the unknown liquid.

The sound speeds and temperature correction coefficients of the liquids included in the data base may be obtained from Shaffs, W., *New Series Group II: Atomic and Molecular Physics*, Vol. 5, *Molecular Acoustics*, (Hellwege, K.H. and Helwege, A.M., Eds.). Springer Verlag. Berlin (1967), but may also be derived experimentally.

Compensation of sound speed based on temperature variation is accomplished by the following relation:

$$V_{TEMP\ CORR} = V_{REF} + C(T_{MEAS} - T_{REF})$$

where:

$V_{TEMP\ CORR}$ is the temperature corrected sound speed;

$V_{REF}$ is the reference sound speed;

C is the temperature correction coefficient of the reference liquid;

$T_{REF}$ is the temperature at which $V_{REF}$ is measured; and $T_{MEAS}$ is the temperature of the unknown liquid.

An example of application of the formula above to find the identity of an unknown liquid where the calculated sound speed ($V_{CALC}$) for an unknown liquid is 1027 m/s and the temperature ($T_{MEAS}$) of the liquid is 25° C. is presented below. The computer program calculates temperature corrected sound speeds for all of the liquids in the data base. Referring to Appendix 1, and realizing that for the sake of simplicity, only two reference liquids are used for this example, it can be seen that trichloroethylene has a sound speed ($V_{REF}$) of 1049 m/s at 20° C. ($T_{REF}$) and a temperature coefficient factor (C) of −4.4 m/(s−°C.). Then for this substance:

$$\begin{aligned} V_{TEMP\ CORR} &= 1049\ m/s\ +\ -4.4\ m/(s - °C.) \times \\ &\quad (25° C. - 20° C.) \\ &= 1027\ m/s \end{aligned}$$

It can be seen that methylene iodide has a sound speed of 973 m/s at 20° C. and a temperature correction factor −1.85 m/(s−°C.). Then for this substance:

$$\begin{aligned} V_{TEMP\ CORR} &= 973\ m/s\ +\ -1.85\ m/(s - °C.) \times \\ &\quad (25° C. - 20° C.) \\ &= 964\ m/s \end{aligned}$$

The program compares the calculated speed of 1027 m/s with a $V_{TEMP\ CORR}$ of 1027 m/s for trichloroethylene and a $V_{TEMP\ CORR}$ of 964 m/s for methylene iodide. The program would identify the unknown liquid as possibly being trichloroethylene, whereas methylene iodide would not be selected. To accommodate experimental error, as for example, ±2%, the program would identify the unknown liquid as possibly being trichloroethylene if the calculated speed was in the range of 1007 to 1047 m/s, as well as any other liquids having temperature corrected sound speeds within this range.

This method and apparatus assumes that the thickness of the container is negligible in comparison to the distance between transducers, and that the speed of sound through the container material is comparable or higher than the speed of sound of the liquid being tested, i.e., the material of container 15 causes no significant delay of the sound pulses. Of course, the distance between transducers 14 and 18 may be determined using other distance measurement tools, as for example, a yardstick, tape measure, or micrometer. This measured distance then may be manually input into computer 22.

The present invention was verified by determining the speed of sound of water having a temperature of 25° C. contained in a six inch diameter coffee can. The calculated speed was 1490 meters/second. This compares favorably with the published value of 1497 m/s at 25° C. A speed of sound determination for methanol was also made. The methanol was contained in a 5 gallon steel drum at a temperature of 25° C. A determination based on sound propagated across the diameter of the drum yielded a sound speed of 1098 m/s, while a measurement made from end to end yielded 1100 m/s. The published value of the speed of sound for methanol is 1103 m/sec at 25° C. A yardstick was used to measure the diameter and length of the drum. An oscilloscope was used to determine the time for the acoustic pulse to traverse the distances used in the speed calculations for both water and methanol. The sound speeds resulting from the above experiments were accurate within 2% of the recognized sound speeds for these materials.

In the examples above, excitation pulse generator included a Krohn-Hite Model 5200A function generator coupled to a Krohn-Hite Model DCA-10 Power Amplifier. Speed was calculated from the quotient: distance/(elapsed time), using a hand-held calculator. It is to be understood that the scope of the invention includes the use of other pieces of equipment than those specifically identified above.

The listing for the computer program implemented in computer 22 is presented, by way of example, in Appendix 1. This program is written and compiled in Microsoft Quickbasic 4.5, and described below. However, it is to be understood computer 22 may be programmed differently and in other languages than as specifically set forth herein.

A database with, for example, 262 entries is read into the array "Dataentry". This database is contained in the DATA statements at the end of the program. The database contains the compound formula, the compound name, the temperature (reference temperature) at which the sound speed measurement was made, the measured sound speed ($V_{REF}$), and the temperature coefficient, "C," of the sound speed. Another array "sscorrected" is set up to hold temperature corrected sound speeds. One of the fields in the database is a "rarity" entry that denotes whether the entry is one of the more common compounds. The opening dialogue, which may be presented by display 32, asks if one wants to search only these common compounds, or the whole database. Then, the temperature information is entered into computer 22. This may be done manually through input device 34, such as a keyboard, or automatically through temperature transducer 28 and A/D converter 30. The temperature corrected sound speeds are then calculated from the entered temperature and the database "Tempcoeff" information. In this case, for each entry in the database, the difference between the measured temperature and the temperature at which the database sound speed was measured is calculated, this difference is multiplied by the temperature correction coefficient, and added to sound speed in the database. These corrected sound speeds are stored in the array "sscorrected." Next, the program compares the calculated sound speed with the temperature corrected sound speeds in the data base by searching the "sscorrected" array for those sound speeds that meet the search criteria. The indexes of the sound speeds that meet the criteria are stored in the array "matches%". The array "matchdata" is created to hold the indexes and the differences between the desired sound speed and the sound speeds of those compounds that meet the search criteria. "Matchdata" is then sorted so that the compounds that are closest to the desired sound speed are output by display 32.

The results of the search are then extracted from the "Dataentry" array using the indexes from the sorted array "matchdata" and printed on the screen. Data that does not have a stored temperature correction coefficient is flagged as being "Not temperature corrected".

Finally a menu is entered that allows the program to be re-entered at different places depending on whether one wants to review the previous search, enter a new sound speed to be searched, or enter a new temperature and sound speed to be searched.

While the present invention has also been described as capable of presenting candidate liquids as the identify of an unknown chemical liquids using speed of sound measurements, the invention may also be used to eliminate chemical liquids as candidates for the unknown liquid. For example, if the sound speed of an unknown liquid is determined to be 1200 m/s at 20° C. Then it can be reliably concluded that the unknown liquid is not acetic acid which has a sound speed of 1164 m/s at 20° C.

The present invention may also be used to confirm the identity of a sample liquid, i.e., to confirm that the liquid is what it is claimed to be. In accordance with the methods described above, a sound pulse is transmitted through the sample liquid and the temperature of the liquid is determined so that the the sound speed through the liquid can be determined. The calculated sound speed then is compared with the the temperature compensated sound speed of the liquid which the sample is supposed to be. If the calculated and reference sound speeds are within a predeterminded interval which allows for experimental error, the sample liquid is probably what it is claimed to be. If the calculated and reference sound speeds are not within the predetermined interval, then the sample liquid is other than what it has been claimed to be.

Obviously, many modifications and variations of the present invention are possible in light of the above teachings. It is therefore to be understood that within the scope of the appended claims, the invention may be practiced otherwise than as specifically described.

Appendix 1

```
TYPE database formula AS STRING * 15

Compound AS STRING * 40

Tempmeas AS SINGLE

Speedmeas AS SINGLE

Tempcoeff AS SINGLE

Rarity AS INTEGER

END TYPE
```

```
numentries% = 262   'present data base has 262 entries
REDIM Dataentry(1 TO numentries%) AS database
'read in the data
FOR i% = 1 TO numentries%
        READ Dataentry(i%).formula, Dataentry(i%).Compound,
Dataentry(i%).Tempmeas, Dataentry(i%).Speedmeas,
Dataentry(i%).Tempcoeff, Dataentry(i%).Rarity
    NEXT i%
REDIM sscorrected(1 TO numentries%)   'set up space for
corrected sound speeds
enter: CLS
INPUT "Search Common Compounds (C) or Entire Database (E)?
", a$
IF UCASE$(a$) = "C" THEN Rare = FALSE ELSE Rare = TRUE INPUT "Temperature of measurement (default is 68 degrees F)
", a$
IF a$ = "" THEN temperature = 68 ELSE temperature = VAL(a$)
'correct the sound speeds for temperature
temperature = (temperature - 32) * 5 / 9    'convert to
celsius scale
'get a corrected sound speed for each element of the
database
FOR i% = 1 TO numentries%
        sscorrected(i%) = Dataentry(i%).Speedmeas +
```

```
        Dataentry(i%).Tempcoeff * (temperature -
Dataentry(i%).Tempmeas)
        NEXT i%
'input the percentage to search within
INPUT "Find matches within what percent? ", percent
percent = percent / 100
REDIM matches%(1 TO numentries%)
search: matchnumber% = 0
INPUT "Sound speed to match: ", sound speed
        'check that sound speed is within desired range
IF sound speed < 400 OR sound speed > 2000 THEN
        PRINT "Sound speed out of range"
        PRINT "Hit any key to re-enter"
        WHILE INKEY$ = "": WEND
        GOTO search
        END IF
'find the matches
'the array matches%() contains the indexes of the data
elements that meet the search criteria
FOR i% = 1 TO numentries%
        IF Rare = TRUE OR Rare = FALSE AND
Dataentry(i%).Rarity = 1 THEN
        IF ABS((sscorrected(i%) - sound speed) / sound speed)
<= percent THEN
                matchnumber% = matchnumber% + 1
```

```
                matches%(matchnumber%) = i%
            END IF
        END IF
        NEXT i%
IF matchnumber% = 0 THEN
        PRINT "No Matches Found"
        WHILE INKEY$ = "": WEND
        GOTO menu:
        END IF
TYPE datamatch
        index AS INTEGER
        difference AS SINGLE
        END TYPE
REDIM matchdata(1 TO matchnumber%) AS datamatch FOR i% = 1 TO matchnumber%
        matchdata(i%).index = matches%(i%)
        matchdata(i%).difference =
ABS(sscorrected(matches%(i%)) - sound speed)
        NEXT i%
CALL SortT(SEG matchdata(1), matchnumber%, 0, 6, 2, -3)
'uses an external sort routine to
        'print the closest matches first

CLS
```

```
PRINT matchnumber%; " MATCHES FOUND"

DO UNTIL INKEY$ <> "": LOOP review: CLS

FOR i% = 1 TO matchnumber%

PRINT Dataentry(matchdata(i%).index).Compound, :

PRINT USING "####"; sscorrected(matchdata(i%).index);

IF Dataentry(matchdata(i%).index).Tempcoeff = 0 THEN

PRINT " Not temperature corrected" ELSE PRINT

IF i% MOD 22 = 0 THEN

PRINT "MORE..."

DO UNTIL INKEY$ <> ""

LOOP

CLS

END IF

NEXT i%

DO UNTIL INKEY$ <> ""

LOOP menu: CLS

PRINT "1-REVIEW LAST SEARCH"

PRINT "2-SEARCH A NEW Sound speed"

PRINT "3-ENTER A NEW TEMPERATURE AND SEARCH A NEW

Soundspeed"

PRINT "4-Exit"
```

```
INPUT action%

SELECT CASE action%

CASE 1

GOTO review:

CASE 2

GOTO search:

CASE 3

GOTO enter:

CASE ELSE

END SELECT
```

DATA C2H4OS,"Thioacetic acid", 20 , 168 , 0,0

DATA C8F16O,"Perfluorcyclooxanonane", 20 , 607 ,-2.81,0

DATA C4HO2F7,"Hydrogenperfluorbutyrate", 30 , 647 ,-2.69,0

DATA C12F27N,"Heptacosafluortributylamine", 20 , 665 ,-2.67,0

DATA C2HF3O2,"Triflouroacetic acid", 20 , 682 ,-3.04,1

DATA C21H8O8F28,"Pentaerythritoltetraperfluorbutyrate", 20 , 824 ,-2.82,0

DATA C2H5J,"Ethyl Iodide", 20 , 876 ,-2.74,1

DATA C2H5Br,"Ethyl Bromide", 20 , 900 ,-3.41,1

DATA CHBr3,"Bromoform", 20 , 931 ,-2.16,0

DATA CCI4,"Carbon Tetrachloride", 20 , 938 ,-3.11,1

```
DATA C6H4Br2,"p-Dibrombenzene", 90 , 949 ,-2.3,0

DATA CH2Br2,"Methylene Bromide", 20 , 963 ,-2.55,1

DATA C14H10,"Anthracene", 250 , 965 ,-2.9,0

DATA C2HBr3O,"Bromal", 20 , 966 , 0,0

DATA C4H9J,"n-Butyliodide", 20 , 972 ,-2.82,0

DATA CH2J2,"Methylene Iodide", 20 , 973 ,-1.85,1

DATA C5H11Br,"n-Amylbromide", 20 , 981 , 0,0

DATA C3H6Br2,"Propylenedibromide", 20 , 995 ,-2.66,0

DATA C24H18,"1-3-5-Triphenylbenzene", 250 , 1000 ,-2.65,0

DATA CHCI3,"Chloroform", 20 , 1001 ,-3.42,1

DATA C4H10O,"Ethyl Ether", 20 , 1006 ,-4.45,1

DATA C2H4Br2,"Ethylene Dibromide", 20 , 1009 ,-2.58,0

DATA C5H12,"i-Pentane", 20 , 1016 , 0,1

DATA C4H9Br,"n-Butylbromide", 20 , 1019 ,-3.34,1

DATA C6H14,"Trimethyllethylmethane", 20 , 1032 ,-5.1,0

DATA CN4O8,"Tetranitromethane", 20 , 1039 , 0,0

DATA C2H2Br4,"1-1-2-2-Tetrabromoethane", 20 , 1041 ,-2.16,0

DATA C2HCl3,"Trichloroethylene", 20 , 1049 ,-4.4,1

DATA C2CI4,"Tetrachlorathylene", 20 , 1053 ,-2.9,1

DATA C2H3CIO,"Acetylchloride", 20 , 1060 , 0,1

DATA C3H9N,"Isopropylamine", 20 , 1089 , 0,1

DATA C3H7CI,"n-Propylchloride", 20 , 1091 ,-3.72,0

DATA CH2CI2,"Methylene Chloride", 20 , 1093 ,-3.9,1

DATA C5H8,"Isoprene", 15 , 1095 ,-5.2,1

DATA C4H10O,"tert. Butanol", 30 , 1098 ,-4.2,1
```

```
DATA C4H4O,"Furan", 30 , 1105 , 0,1
DATA C18H12,"Triphenylene", 250 , 1108 ,-2.6,0
DATA C8H18,"i-Octane", 20 , 1111 , 0,1
DATA C6H14O,"Di-n-propylether", 20 , 1112 , 0,0
DATA C2HCI5,"Pentachlorathane", 20 , 1113 , 0,0
DATA C6H5J,"Iodobenzene", 20 , 1114 ,-2.7,0
DATA CH4O,"Methanol", 20 , 1120 ,-3.25,1
DATA C3H5CI,"Allylchloride", 20 , 1132 ,-3.9,0
DATA C5H10O2,"i-Propylacetate", 20 , 1133 ,-4.43,0
DATA C4H9CI,"n-Butylchloride", 20 , 1140 ,-4.07,0
DATA C6H4CI2,"p-Dichlobenzene", 60 , 1142 ,-3.1,0
DATA C6H15N,"Triathylamine", 20 , 1143 ,-4.5,0
DATA C4H11N,"Diethyl amine", 20 , 1150 ,-3.8,0
DATA C4H6O2,"Vinylacetate", 20 , 1152 , 0,1
DATA C7H16,"n-Heptane", 20 , 1154 ,-4.14,1
DATA CS2,"Carbon Disulfide", 20 , 1157 ,-3.2,1
DATA C2H6O,"Ethanol", 20 , 1159 ,-3.15,1
DATA C3H6O2,"Ethyl formate", 20 , 1160 ,-4.23,0
DATA C5H8,"Cyclopentene", 30 , 1160 , 0,0
DATA C3H6CI2,"Propylenedichloride", 20 , 1162 ,-3.76,0
DATA C2H4O2,"Acetic Acid", 20 , 1164 , 0,1
DATA C7H7Br,"p-Bromtolulene", 30 , 1164 ,-3.03,0
DATA C2H2CI4,"1-1-2-2-Tetrachloroethane", 20 , 1170 ,-3.17,1
DATA C3H8O,"i-Propanol", 20 , 1170 ,-4,1
DATA C6H5Br,"Bromobenzene", 20 , 1170 ,-3.12,0
```

```
DATA C4H8O2,"Ethyl acetate", 20 , 1177 ,-4.88 ,1
DATA C10H14,"1-2-4-5-Tetramethylbenzene", 80 , 1177 ,-3.6,0
DATA C7H14O2,"i-Amylacetate", 30 , 1179 , 0,0
DATA C3H6O2,"Methylacetate", 20 , 1182 ,-4.73,1
DATA C5H10,"Cyclopentane", 30 , 1182 , 0,0
DATA C6H12O2,"i-Butylacetate", 20 , 1182 ,-3.98,0
DATA C8H17Br,"n-Octylbromide", 20 , 1182 , 0,0
DATA C5H10O2,"Ethylpropionate", 20 , 1183 ,-4.2,0
DATA C3H6O,"Acetone", 20 , 1189 ,-4.3,1
DATA C6H5F,"Fluorbenzene", 20 , 1189 ,-4.17,0
DATA C7H14O2,"Ethyl valerianate", 20 , 1189 ,-3.95,0
DATA C7H14O2,"i-Butylpropionate", 20 , 1189 ,-3.7,0
DATA C7H13Br,"p-methylclclohexylbromide", 20 , 1189 ,-3.28,0
DATA C3H4O,"Acrolein", 20 , 1190 , -4.1,0
DATA C4H8O2,"Propyl formate", 20 , 1192 ,-4.4,0
DATA C6H12O2,"Paraldehyde", 20 , 1192 ,-4.2,0
DATA C8H18,"n-Octane", 20 , 1192 ,-4.22,1
DATA C713Br,"m-methylcyclohexylbromide", 20 , 1194 ,-3.33,0
DATA C6H12O2,"Ethylbutyrate", 20 , 1197 ,-4.1,0
DATA C5H10O2,"n-Propylacetate", 20 , 1198 ,-4.83,0
DATA C6H14O,"4-Methylpentanol", 30 , 1201 , 0,0
DATA C14H12,"Stilbene", 140 , 1201 ,-3,0
DATA C7H7Br,"o-Bromotolulene", 20 , 1205 ,-3.07,0
DATA C8H14,"4-Octyne", 20 , 1205 , 0,0
DATA C13H10,"Fluorene", 140 , 1205 ,-3.1,0
```

```
DATA C2H4O,"Acetaldehyde", 0 , 1207 ,-4.7 ,1
DATA C12H10O,"Diphenylether", 100 , 1210 ,-3.31,0
DATA C4H6O,"Methacrolein", 20 , 1211 ,-4.4,0
DATA C4H10O,"i-Butanol", 20 , 1212 ,-3.5,1
DATA C5H10O2,"Butyl formate", 20 , 1215 ,-4.1,0
DATA C2H4CI2,"Ethylene Chloride", 20 , 1216 ,-3.95,1
DATA C3H6O,"Allylalcohol", 30 , 1216 , 0,0
DATA C4H8O,"Methyl ethyl ketone", 20 , 1217 ,-4.29,1
DATA C5H10O,"Diethylketone", 25 , 1218 , 0,1
DATA C6H13CI,"n-Hexylchloride", 20 , 1221 , 0,0
DATA C3H8O,"n-Propanol", 20 , 1222 ,-3.66,1
DATA C6H12O2,"Amyl formate", 20 , 1223 ,-4.23,0
DATA C6H12O2,"n-Butylacetate", 20 , 1226 ,-4.05,0
DATA C7H14O2,"n-Butylpropionate", 20 , 1227 ,-4 ,0
DATA C10H20O2,"n-Amyl-n-valerianate", 20 , 1228 ,-3.7,0
DATA C8H16O2,"Amylpropionate", 20 , 1231 ,-4.05,0
DATA C7H16O,"2-4-Dimethylpentanol-3", 30 , 1241 , 0,0
DATA C4H10O4S,"Di-ethyl sulfate", 20 , 1244 , 0,0
DATA C7H14O,"Di-n-propylketone", 25 , 1246 , 0,0
DATA C9H18O2,"n-Amylbutyrate", 20 , 1246 ,-3.9,0
DATA C10H8,"Naphthalene", 100 , 1246 ,-3.4,0
DATA C7H14,"Methylcyclohexane", 20 , 1247 , 0,0
DATA C4H6O3,"Acetic Anhydride", 30 , 1249 ,-3.2,1
DATA C7H8O2,"Guajacol", 100 , 1252 ,-3.7,0
DATA C2H6O4S,"Dimethylsulfate", 20 , 1255 , 0,0
```

```
DATA C4H8O,"Tetrahydrofuran", 30 , 1255 , 0,1
DATA C4H8O,"Ethyl vinyl ether",-25 , 1256 ,-4.9,0
DATA C4H6O2,"Diacetyl", 20 , 1259 , 0,0
DATA C5H12O,"i-Amylalcohol", 20 , 1260 ,-3.42,0
DATA C4H10O,"n-Butanol", 20 , 1263 ,-3.56,0
DATA C5H8O,"Dihydropyran", 30 , 1264 , 0,0
DATA C7H16O,"Heptanol-2", 30 , 1267 , 0,0
DATA C3H5N,"n-Propionitrile", 20 , 1271 , 0,0
DATA C12H10,"Diphenyl", 100 , 1271 ,-3.55,0
DATA C6H6O,"Phenol", 100 , 1274 ,-3.24,1
DATA C16H10,"Pyrene", 160 , 1275 ,-2.61,0
DATA C6H14O,"2-Ethylbutanol", 30 , 1277 , 0,0
DATA C6H12,"Cyclohexane", 20 , 1277 ,-4.6,0
DATA C8H17CI,"n-Octylchloride", 20 , 1280 , 0,0
DATA C12H8O,"Diphenyleneoxide", 100 , 1282 ,-3.05,0
DATA C4H6O,"Crotonaldehyde", 20 , 1288 ,-4.08,0
DATA C6H5CI,"Chlorbenzene", 20 , 1289 ,-3.73,0
DATA C6H4CI2,"m-Dichlorbenzene", 20 , 1295 , 0,0
DATA C6H4CI2,"o-Dichlorbenzene", 20 , 1296 ,-3.3,0
DATA C2H3N,"Acetonitrile", 20 , 1300 ,-4,1
DATA C10H18,"5-Decyne", 20 , 1300 , 0,0
DATA C4H4S,"Thiophene", 20 , 1301 ,-4.1,0
DATA C6H3CI3,"1-2-4-Trichlorbenzene", 20 , 1301 , 0,0
DATA C7H7NO2,"p-Nitrotolulene", 70 , 1301 ,-3.7,0
DATA C6H10,"Cyclohexane", 20 , 1305 ,-5.4,0
```

```
DATA C8H15O,"2-Ethyl-3-propylacrolein", 25 , 1306 ,-3.8,0
DATA C7H7CI,"p-Chlortolulene", 20 , 1308 ,-3.6,0
DATA C10H14O,"Thymol", 60 , 1308 , 0,0
DATA C6H10O,"Mesityloxide", 20 , 1310 , 0,0
DATA C10H20O2,"Octylacetate", 20 , 1310 ,-4.2,0
DATA C7H7CI,"m-Chlortolulene", 20 , 1316 ,-3.63,0
DATA C13H10O,"Benzophenon", 100 , 1316 ,-3,0
DATA C6H5NO3,"o-Nitrophenol", 70 , 1318 ,-3.6,0
DATA C10H21CI,"n-Decylchloride", 20 , 1318 , 0,0
DATA C6H11CI,"Cyclohexylchloride", 20 , 1319 , 0,0
DATA C7H7CI,"o-Chlortolulene", 20 , 1319 ,-3.7,0
DATA C6H6,"Benzene", 20 , 1324 ,-4.6,1
DATA C4H10O2,"Ethyl-ethanolic ether", 20 , 1325 ,-4.1,0
DATA C11H24O,"5-Athylnonanol-2", 30 , 1327 , 0,0
DATA C7H8,"Tolulene", 20 , 1328 ,-4.3,1
DATA C19H16,"Triphenylmethane", 100 , 1329 ,-3.2,0
DATA C8H10,"p-Xylene", 20 , 1334 ,-4.3,1
DATA C14H10,"Phenanthrene", 120 , 1336 ,-3,0
DATA C8H10,"Ethylbenzene", 20 , 1338 ,-3.8,0
DATA C10H19O,"l-Linalool", 20 , 1341 , 0,0
DATA C4H6O,"Methylvinylketone", 0 , 1342 ,-4.4,0
DATA C9H12,"i-Ppropylbenzene", 20 , 1342 ,-3.65,0
DATA C8H10,"m-Xylene", 20 , 1343 ,-4.1,1
DATA CH3NO2,"Nitromethane", 20 , 1346 ,-4.05,1
DATA C4H9N,"Pyrrolidine", 30 , 1347 , 0,0
```

```
DATA C10H14,"n-Butylbenzene", 20 , 1351 ,-3.6,0
DATA C8H8,"Styrene", 20 , 1354 , 0,0
DATA C11H22O,"Methyl-n-nonylketone", 20 , 1356 , 0,0
DATA C7H6O2,"Furacrolein", 60 , 1360 ,-3.3,0
DATA C10H18,"Dicyclopentyl", 30 , 1361 , 0,0
DATA C9H12,"Mesitylene", 20 , 1362 ,-4.8,0
DATA C16H34,"n-Hexadecane", 20 , 1363 ,-3.78,0
DATA C8H10,"o-Xylene", 20 , 1364 ,-3.8,1
DATA C14H14,"Dibenzyl", 60 , 1364 ,-3.2,0
DATA C4H8O2,"1-4-Dioxane", 20 , 1366 ,-4.32,0
DATA C7H5ClO,"Benzoylchloride", 20 , 1366 ,-3.5,0
DATA C9H12,"Pseudocumene", 20 , 1368 , 0,0
DATA C2H5ClO,"Ethylene chlorihydrin", 20 , 1372 ,-3,0
DATA C3H3NS,"Thiazole", 30 , 1372 , 0,0
DATA C9H12,"Hemellithene", 20 , 1372 , 0,0
DATA C10H7Br,"Bromnaphthalene", 20 , 1372 ,-3.05,0
DATA C7H12O,"m-Methylcyclohexanone", 20 , 1373 , 0,0
DATA C9H12,"1-8-Nonadiyne", 20 , 1375 , 0,0
DATA C5H8O2,"Acetylacetone", 20 , 1383 , 0,0
DATA C8H8O2,"Furfuralacetone", 50 , 1383 ,-3.4,0
DATA C7H7NO3,"p-Nitroanisole", 70 , 1384 ,-3.7,0
DATA C12H26O,"n-Dodecanol", 30 , 1388 , 0,0
DATA C8H6,"Phenylacetylene", 20 , 1389 , 0,0
DATA C10H18O,"d-Citronellal", 20 , 1392 , 0,0
DATA C5H11N,"Piperidine", 20 , 1400 , 0,1
```

```
DATA C7H14O,"p-Methylcyclohexanol", 20 , 1403 , 0,0

DATA C9H10,"Hydrindene", 20 , 1403 , 0,0

DATA C5H4O3,"Citraconsaureanhydrid", 20 , 1414 , 0,0

DATA C6H10O2,"Acetonylaceton", 20 , 1416 , 0,0

DATA C4H8OS,"1-4-Thioxane", 30 , 1420 , 0,0

DATA C7H7CI,"Benzylchloride", 20 , 1420 , 0,0

DATA C12H22,"Dicyclohexyl", 30 , 1422 , 0,0

DATA C7H8O,"Anisole", 20 , 1425 ,-3.6,1

DATA C11H14O2,"Benzylbutyrate", 20 , 1432 ,-3.8,0

DATA C13H20O,"Jonone", 20 , 1432 , 0,0

DATA C5H6O2,"Furfurylalkohol", 30 , 1434 , 0,0

DATA C10H7NO2,"Nitronaphthalene", 70 , 1435 ,-3.1,0

DATA C7H14O,"o-Methylcyclohexanol", 20 , 1436 , 0,0

DATA C4H5N,"Pyrrole", 30 , 1438 , 0,0

DATA C10H12O2,"Benzylpropionate", 20 , 1440 ,-3.88,0

DATA C5H5N,"Pyridine", 20 , 1441 ,-4.14,1

DATA C10H16O,"Citral", 20 , 1442 , 0,0

DATA C7H12O,"o-Methylcyclohexanone", 20 , 1443 , 0,0

DATA C6H12O,"Cyclohexanol", 30 , 1444 ,-4,0

DATA C13H12,"Diphenylmethane", 40 , 1448 ,-3.3,0

DATA C15H20O,"Hexylcinnamonaldehyde", 25 , 1448 ,-3.4,0

DATA C6H10O,"Cyclohexanone", 20 , 1449 , 0,0

DATA C4H9NO,"Morpholine", 20 , 1461 , 0,0

DATA C9H10O2,"Benzylacetate", 20 , 1463 ,-3.93,0

DATA C4H10O2,"Tetrahydrofurfurylalkohol", 30 , 1468 , 0,0
```

```
DATA C8H8O2,"Benzylformate", 20 , 1472 ,-4.05,0
DATA C6H14O3,"Diethyleneglycol-monoethyl ether", 20 , 1473 ,
0,0
DATA C7H7NO2,"o-Nitrotolulene", 20 , 1473 ,-3.65,0
DATA C6H6N2O2,"o-Nitroaniline", 80 , 1475 ,-3.1,0
DATA C6H5NO2,"Nitrobenzene", 20 , 1475 ,-3.4,1
DATA C9H8,"Indene", 20 , 1475 , 0,0
DATA C10H14O,"Carvacrol", 20 , 1475 , 0,0
DATA C12H16,"Phenylcyclohexane", 20 , 1475 ,-3.65,0
DATA C3H4O3,"Pyruvic acid", 20 , 1476 ,-3.3,0
DATA C3H7NO,"Dimethylformamid", 20 , 1478 ,-3.62,1
DATA C7H6O,"Benzaldehyde", 20 , 1479 , 0,1
DATA C7H9N,"p-Tolulidine", 50 , 1480 ,-3.8,0
DATA C7H7NO2,"m-Nitrotolulene", 20 , 1481 ,-3.6,0
DATA C10H7CI,"Chlornaphthalene", 20 , 1481 , 0,0
DATA C10H15N,"Diethylaniline", 20 , 1482 , 0,0
DATA C57H104O6,"Triolein", 20 , 1482 , 0,0
DATA C10H12,"Tetralin", 20 , 1484 ,-3.5,0
DATA C10H14N2,"Nicotine", 20 , 1491 , 0,0
DATA C8H8O,"Acetophenone", 20 , 1496 , 0,1
DATA C9H10O,"Ethylphenylketone", 20 , 1498 , 0,0
DATA C7H8O,"m-Cresol", 20 , 1500 ,-3.5,1
DATA C6H6CIN,"o-Chloraniline", 20 , 1506 ,-3.5,0
DATA C12H11N,"Diphenylamine", 60 , 1508 ,-3.4,0
DATA C8H111N,"Dimethylaniline", 20 , 1509 , 0 ,0
```

```
DATA C8H10O,"Phenylethanol", 30 , 1513 , 0,0
DATA C10H12O,"Benzylacetone", 20 , 1514 , 0 ,0
DATA C9H12O,"Phenylpropanol", 30 , 1523 , 0,0
DATA C7H9NO,"p-Anisidine", 70 , 1530 ,-4,0
DATA C4H10O2,"1-3-Butandiol", 20 , 1539 , 0,0
DATA C7H8O,"Benzylalcohol", 20 , 1540 ,-3.2,1
DATA C7H8O,"o-Cresol", 20 , 1541 ,-3.8,1
DATA C6H6ClN,"m-Chloraniline", 20 , 1550 ,-3.4,0
DATA C10H9N,"Chinaldin", 20 , 1575 , 0,0
DATA C7H9N,"Benzylamine", 30 , 1577 , 0,0
DATA C2H5O3N,"Nitroethanol", 20 , 1578 , 0,0
DATA C9H8O,"Cinnaminaldahyde", 20 , 1580 ,-3.5,0
DATA C7H9N,"N-Methylaniline", 20 , 1586 , 0,0
DATA C15H17N,"Athylbenzylaniline", 20 , 1586 , 0,0
DATA C7H9N,"m-Toluidine", 20 , 1594 ,-3.5,0
DATA C4H10O3,"Di ethanolic ether", 20 , 1598 , 0,0
DATA C9H7N,"Chinoline", 20 , 1600 ,-4.78,0
DATA C8H18O5,"Tetra ethylene glycol", 20 , 1601 , 0,0
DATA C4H10O2,"1-4-Butandiol", 20 , 1616 , 0,0
DATA C7H9N,"o-Toluidine", 20 , 1618 ,-3.9,0
DATA CH3NO,"Formamid", 25 , 1622 , 0,1
DATA C6H14O4,"Triethylethyleneglycol", 20 , 1646 , 0,0
DATA C6H7N,"Aniline", 20 , 1659 ,-4.05,1
DATA C2H6O2,"Ethylene Glycol", 20 , 1667 ,-2.5,1
DATA C6H8N2,"Phenylhydrazine", 20 , 1738 , 0,0
DATA C2H7NO,"2-aminio-ethanol", 20 , 1741 , 0,0
DATA C3H8O3,"Glycerol", 20 , 1895 ,-1.9,1
DATA H2O,"Water",25,1497,2.4,1
END
```

We claim:

1. An apparatus for identifying an unknown liquid, comprising;

first means acoustically coupled to said liquid for generating an acoustic pulse through said unknown liquid, said first means including:
   an excitation pulse generator for generating an electric pulse; and
   a first acoustic transducer coupled to receive said electric pulse from said pulse generator and for generating said acoustic pulse through said unknown liquid, said transducer being acoustically coupled to said unknown liquid at a first location;

second means acoustically coupled to said unknown liquid and operably disposed for receiving said acoustic pulse, said second means including:
   a second acoustic transducer acoustically coupled to said unknown liquid at a second location different than said first location, said second transducer operatively disposed to receive said acoustic pulse;

third means operatively coupled to said first and second means for determining the time required for said acoustic pulse to traverse a predetermined distance through said unknown liquid and for providing an output corresponding to said time;

fourth means for determining the temperature of said unknown liquid and providing an output corresponding to said temperature;

a computer operably coupled to receive said outputs from said third and fourth means for determining the speed of said acoustic pulse through said unknown liquid and for comparing said speed of said acoustic pulse with the sound speed of at least one known liquid at said temperature, said computer including a data base comprising a reference sound speed for each said known liquid at a reference temperature, where said sound speed of said known liquid at said temperature is determined in accordance with the relation:

$$V_{TEMP\ CORR} = V_{REF} + C(T_{MEAS} - T_{REF})$$

where:
   $V_{TEMP\ CORR}$ is a sound speed of one said known liquid at said temperature;
   $V_{REF}$ is said reference sound speed;
   C is a temperature correction coefficient of said known liquid; and
   $T_{MEAS}$ is said temperature of said unknown liquid;
   a display for presenting the identity of each said known liquid having a sound speed within a predetermined interval of said speed of said acoustic pulse; and
   a gated clock operatively coupled to said pulse generator and to said second acoustic transducer for providing an output to said computer corresponding to the time required for said acoustic pulse to travel from said first acoustic transducer to said second acoustic transducer.

2. The apparatus of claim 1 which further includes:
   a caliper having a first end to which said first acoustic transducer is mounted and a second end to which said second acoustic transducer is mounted; and
   a displacement transducer mounted to said caliper and operably coupled to provide an output signal to said computer corresponding to the distance between said first and second acoustic transducers.

* * * * *